US006267966B1

(12) United States Patent
Baillie

(10) Patent No.: US 6,267,966 B1
(45) Date of Patent: Jul. 31, 2001

(54) **VACCINE PRODUCTION OF THE *BACILLUS ANTHRACIS* PROTECTIVE ANTIGEN**

(75) Inventor: Leslie W J Baillie, Salisbury (GB)

(73) Assignee: The Secretary of State for Defence, Farnborough (GB)

( * ) Notice: Subject to any disclaimer, the term of this patent is extended or adjusted under 35 U.S.C. 154(b) by 0 days.

(21) Appl. No.: 09/242,846

(22) PCT Filed: Aug. 26, 1997

(86) PCT No.: PCT/GB97/02288

§ 371 Date: Feb. 25, 1999

§ 102(e) Date: Feb. 25, 1999

(87) PCT Pub. No.: WO98/08952

PCT Pub. Date: Mar. 5, 1998

(30) Foreign Application Priority Data

Aug. 30, 1996 (GB) .................................. 9618107

(51) Int. Cl.[7] .................................. A61K 39/295
(52) U.S. Cl. .................................. 424/200.1; 424/93.46; 424/93.462; 424/184.1; 424/235.1; 424/236.1; 435/69.3; 435/252.3; 435/252.31; 435/320.1; 435/480; 435/485; 530/825; 536/23.7
(58) Field of Search .................... 424/93.46, 93.462, 424/184.1, 200.1, 235.1, 236.1; 435/69.3, 252.3–252.31, 320.1, 480, 485; 530/300, 350, 806, 825; 536/23.7

(56) References Cited

U.S. PATENT DOCUMENTS 5,591,631 * 1/1997 Leppla et al. ..................... 435/252.3

OTHER PUBLICATIONS

Baillie et al. Evaluation of *Bacillus subtilis* strain IS53 for the production of *Bacillus anthracis* pretective antigen. Letters in Applied Microbiology. vol. 19 (1994) pp. 225–227.*

Ivins et al. Cloning and expression of the *Bacillus anthracis* protective antigen gene in *Bacillus subtilis*. vol. 54, No. 2 (1986) pp. 537–542.*

Riffkin et al. A single amino–acid change between the antigenically different extracellular serine protease V2 and B2 from *Dichelobacter nodusus*. Gene. vol. 167 (1995) pp. 279–283.*

Ivins Be et al: "Cloning and expression of the *Bacillus anthracis* protective antigen gene in *Bacillus subtillis*." Infect Immun, Nov. 1986, 54 (2) P537–42, United States, SP002049155 see whole document.

Miwa Y et al: "Determination of the CIS Sequence Involved in Catabolite Repression of the *Bacillus–Subtilis* GNT Operon Implication of a Consensus Sequence in Catabolite Repression in the Genus Bacillus" Nucleic Acids Research, 18 (23). 1990. 7049–7054., xp002049156 see whole document.

Kraus A et al: "Analysis of CcpA mutations defective in carbon catabolite repression in *Bacillus megaterium*." FEMS Microbiol Lett, Aug. 1, 1997, 153 (1) P221–6, Netherlands, XP002049157 see whole document.

Strauch Ma: "AbrB modulates expression and catabolite repression of a *Bacillus subtillis* ribose transport operon." J Bacterio;, Dec. 1995, 177 (23) P6727–31, United States, XP002049153 see the whole document.

Huect CJ et al: "Analysis of a CIS–Active Sequence Mediating Catabolite Repression in Gram–Positive Bacteria" Research In Microbiology, 1994, 145, 503–518, XP002049154 see whole document.

* cited by examiner

*Primary Examiner*—Jeffrey Stucker
*Assistant Examiner*—Ulrike Winkler
(74) *Attorney, Agent, or Firm*—Nixon & Vanderhye P.C.

(57) ABSTRACT

Methods of preparing recombinant *Bacillus anthracis* protective antigen or a variant or fragment thereof for use in vaccines is disclosed. The protein is expressed in a recombinant microorganism which comprises a sequence which encodes PA or said variant or fragment thereof wherein either (i) a gene of the microorganism which encodes a catabolic repressor protein and/or AbrB is inactivated, and/or (ii) wherein a region of the PA sequence which can act as a catabolic repressor binding site and/or an AbrB binding site is inactivated. Useful quantities of protein are obtainable from these organisms.

33 Claims, 2 Drawing Sheets

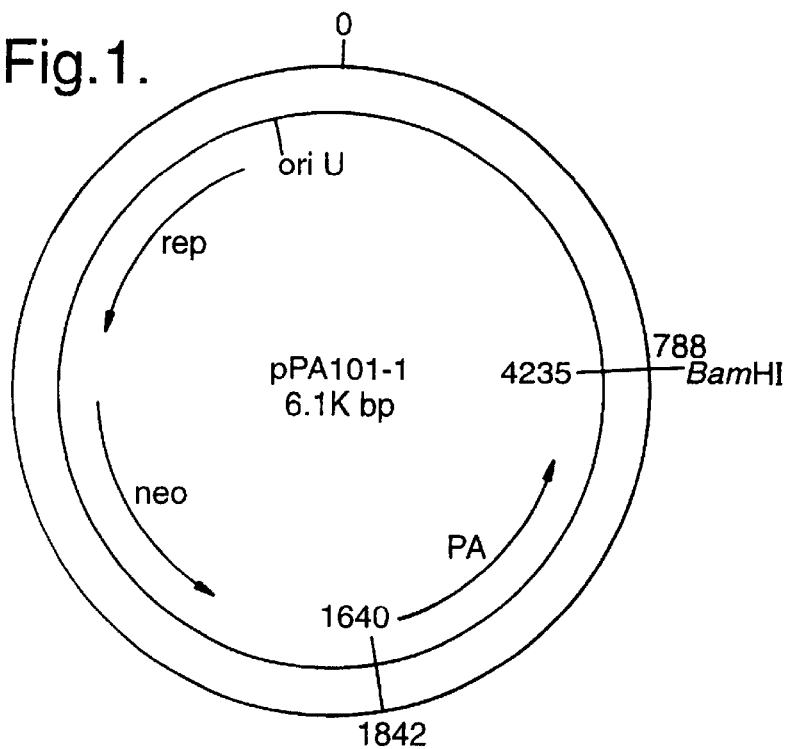
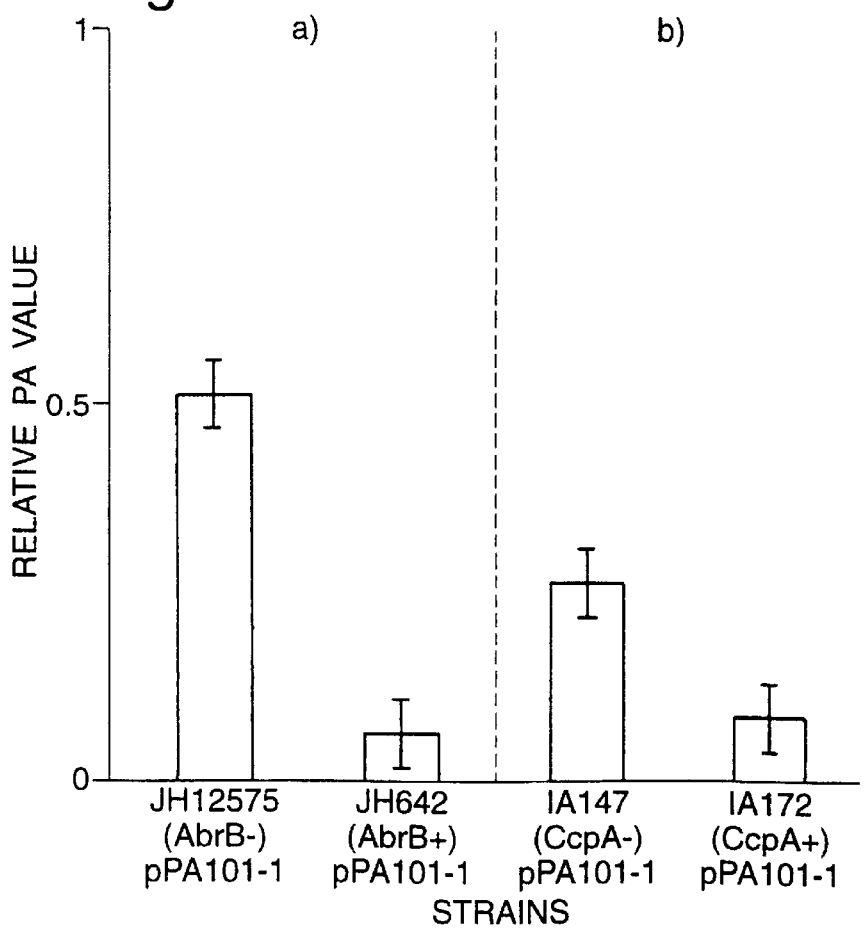

ns application is a national stage application of PCT/GB97/02288, filed Aug. 26, 1997.

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 300 base pairs
      (B) TYPE: nucleic acid
      (C) STRANDEDNESS: double
      (D) TOPOLOGY: linear (xi) SEQUENCE DESCRIPTION: SEQ ID NO: 1:

```
TATAAATTCT TTTTTATGTT ATATATTTAT AAAAGTTCTG TTTAAAAAGC CAAAAATAAA      60

TAATTATCTC TTTTTATTTA TATTATATTG AAACTAAAGT TTATTAATTT CAATATAAT     120

TAAATTTAAT TTTATACAAA AAGGAGAACG TATATGAAAA AACGAAAAGT GTTAATACC     180

TTAATGGCAT TGTCTACGAT ATTAGTTTCA AGCACAGGTA ATTTAGAGGT GATTCAGGC     240

GAAGTTAAAC AGGAGAACCG GTTATTAAAT GAATCAGAAT CAAGTTCCCA GGGGTTACT     300
```

(2) INFORMATION FOR SEQ ID NO: 2:

(i) SEQUENCE CHARACTERISTICS:
      (A) LENGTH: 14 base pairs
      (B) TYPE: nucleic acid
      (C) STRANDEDNESS: double
      (D) TOPOLOGY: linear (xi) SEQUENCE DESCRIPTION: SEQ ID NO: 2:

```
-continued

TGWNANCGNT NWCA                                                  14

(2) INFORMATION FOR SEQ ID NO: 3:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO: 3:

WAWWTTTWCA AAAAAW                                                16
```

VACCINE PRODUCTION OF THE *BACILLUS ANTHRACIS* PROTECTIVE ANTIGEN

This application is a national stage application of PCT/GB97/02288, filed Aug. 26, 1997.

The present invention relates to the production of immunogenic proteins such as the protective antigen (PA) of *Bacillus anthracis* using recombinant DNA technology, to expression vectors and hosts used in the production process and to methods of their preparation.

*Bacillus anthracis*, the causative agent of anthrax possesses two main virulence factors, a poly-D-glutamic capsule and a tripartite protein toxin. PA, the non-toxic, cell-binding component of the toxin, is the essential component of the currently available human vaccine. The vaccine is usually produced from batch cultures of the Sterne strain of *B. anthracis*, which although avirulent, is still required to be handled as a Class III pathogen. In addition to PA, the vaccine contains small amounts of the anthrax toxin moieties, edema factor and lethal factor, and a range of culture derived proteins. All these factors contribute to the recorded reactogenicity of the vaccine in some individuals. The vaccine is expensive and requires a six month course of four vaccinations. Futhermore, present evidence suggests that this vaccine may not be effective against inhalation challenge with certain strains (M. G. Broster et al., Proceedings of the International Workshop on Anthrax, Apr. 11–13, 1989, Winchester UK. Salisbury med Bull Suppl No 68, (1990) 91–92).

Previous workers have attempted to produce PA in *Escherichia coli* (M. H. Vodkin et al., Cell, (1983)34, 693–697) and *Salmonella typhimurium* (N. M. Coulson et al., Vaccine (1994) 12, 1395–1401) but for reasons which are not known, the level of production of PA was low in these organisms.

*B. subtilis* is a harmless bacterium usually found in the environment. The possibility of using a genetically transformed *B. subtilis* to produce just PA, without other, undesirable components of the anthrax toxin, and without the need for rigorous containment has previously been proposed (B. E. Ivins et al., Infection and Immunity (1986), 54, 537–542). In particular, the gene encoding the protective antigen moiety of the tripartite exotoxin of *B. anthracis* was cloned into *B. subtilis* IS53 using the plasmid vector pUB110. Two clones, PA1 and PA2, were obtained, both of which produced more PA in liquid cultures than the Sterne strain of *B.anthracis* with levels of up to 41.9 mg/l being achieved. However, the organism also produced proteolytic enzymes, albeit in low quantities, which degraded the PA and made subsequent purification difficult.

This PA expression system (*B. subtilis* IS53 (pPA102)) has been evaluated (L. W. J. Baillie et al., Lett Appl. Microbiol. (1994) 19, 225–227). The system suffered from a down-regulation of the PA gene in early fermentation and was not proposed for large-scale production of PA antigen.

For production on an industrial scale, for example in vaccine production, it is important to maximise yields of protein for cost reasons. It is also helpful to obtain protein in the form of full length protein as this will be easier to purify than a selection of proteolytic fragments. The applicants have identified a number of expression factors which lead to improved levels of PA production.

Hence the present invention provides a recombinant microorganism which is able to express *Bacillus anthracis* protective antigen or a variant or fragment thereof which is able to generate an immune response in a mammal, said microorganism comprising a sequence which encodes PA or said variant or fragment thereof wherein either (i) a gene of said microorganism which encodes a catabolic repressor protein and/or AbrB is inactivated,and/or (ii) a region of the said PA sequence which can act as a catabolic repressor binding site is inactivated; and/or (iii) a region of the said PA sequence which can act as an AbrB binding site is inactivated.

Variants and fragments of PA must be able to produce an immune response in a mammal to whom they are administered. The immune response is suitably protective against infection by *Bacillus anthracis* although the protective effect may be seen only after repeated applications, as would be determinable by methods known in the art. Variants comprise peptides and proteins which resemble PA in their effect, but have different amino acid sequence. For example, variants may be 60% homologous to PA protein, suitably 80% homologous and more particularly at least 90% homologous. Fragments are suitably peptides which contain at least one antigenic determinant of PA, or variants thereof.

As used herein, the expression "functional equivalent" refers to moities such as nucleotide sequences or proteins, which although different to the reference moieties in certain respects, qualitatively fulfill the same biological function.

A suitable microorganism for use as a host organism is a strain of *Bacillus subtilis*. Suitable strains are available from various sources including the Bacillus Genetic Stock Center, The Ohio State University, Columbus, Ohio, USA from where strains such as IA147 and IA172 may be obtained. Additional strains are described in the literature, for example by Perego et al., Molecular Microbiology, (1988) 2, 689–699 where strains JH642 and JH12575 are described.

Preferably however, the microorganism of the invention comprises a strain which produces little or no proteases, since PA is very susceptible to decomposition by protease. A particularly preferred strain of *Bacillus subtilis* is a protease deficient strain. One such strain is *B.subtilis* WB600. This organism has been engineered to be deficient in six extracellular proteases (Xu-Chu Wu et al., J. Bacteriol. (1991) 173, 4952–4958). This strain is able to produce high yields of PA, for example of up to 40 mg/l which allowed the development of a purification strategy.

Catabolite repression of gene expression involves the trans-acting factors Catabolite control protein A (CcpA) and the phosphocarrier protein Hpr (Saier et al., Microbiology (1996), 142, 217–230). It has been proposed that CcpA binds to a catabolite-responsive element sequence in the control region of catabolite-sensitive operons and prevents transcription when glucose is present (Henkin et al. Molecular Microbiology (1991) 5, 575–584).

AbrB is a transition state regulator which prevents inappropriate gene expression during vegetative growth. Like CcpA, AbrB binds to DNA and prevents gene transcription (Strauch et al., J. of Bacteriology (1995), 177, 6999–7002).

Comparison of the level of PA expression from wildtype and mutant strains revealed that PA is subject to catabolite repression and AbrB regulation. In particular, it was found that PA levels from pPA101-1 are three fold higher in a ccpA mutant than in an otherwise isogenic parent, and eight fold higher in an abrB mutant. Thus, the introduction of mutations affecting catabolite repression and growth phase regulation into strains which are not deficient in these may result in an increase in the yield of PA in this host-vector system.

Screening of the PA control region for potential catabolite repressor binding sites revealed a region with 81% homology which started 37 bases downstream of the translational start point (see FIG. 3 hereinafter). Screening with the abrB consensus sequence produced three regions which showed between 82–89% homology. The closest match was for a region which included the P2 translational start point and overlapped the ribosome binding site. Thus PA repression may be due to Catabolite control protein A (CcpA) and AbrB binding directly to these target sequences.

Suitably therefore, one or both of these sites are inactivated so as to increase the expression of PA. Inactivation may be effected by for example by mutation of the relevant site. The skilled person would be able to produce these, for example using site directed mutagenesis, and test for the required inactivation using routine techniques.

Preferably however, these activities are inhibited by inactivation of the gene which produce the relevant proteins (e.g. AbrB or CcpA). Either a host strain which is deficient in the genes which produce either or both or these proteins are employed, or one or both of the genes of the host strain are inactivated. Suitable inactivation techniques include insertion mutagenesis, where preferably a selection marker gene is inserted into the relevant gene in the host DNA using conventional methods. A suitable selection marker gene is Tn917 which encodes the antibiotic marker erythromycin.

Catabolite repressor activity may additionally or alternatively be inhibited by controlling the growth media in which the organisms are cultured. This control may be effected by excluding certain sugars such as glucose which invoke this activity, and using alternative carbon sources such as glycerol and such methods form a further aspect of the invention.

*Bacillus anthracis* protective antigen may be obtained by culturing a recombinant microorganism as described above and such a process forms a further aspect of the invention. In a preferred embodiment, the microorganisms of the invention are cultured under conditions in which catabolite repressor activity is minimised as described above.

The repression of gene expression by amino acid mixtures has been described (Atkinson et al., Journal of Bacteriology, (1990) 172, 4758–4765). Although the mechanism of this repression is not yet fully understood, recent work has shown that a DNA binding protein called CodY is involved in the amino acid repression of a number of genes (Serror et al. Proceedings of the 8th International Conference on Bacilli, (1995) July 8–12, Stanford, USA, p39. There is some evidence from growth studies with *B.anthracis* to suggest that PA expression may be subject to amino acid repression (Bartkus et al., Infection and Immunity, (1989) 57, 2295–2300; S. H. Leppla, SourceBook of Bacterial Toxins, ed. J. E. Alouf and J. H. Freer, pp277–302, Academic Press).

The amino acid composition of the media has been found to influence the level of PA expression and therefore the organism is preferably cultured in the presence of at least one amino acid which stimulates PA expression. The levels of said amino acid may be boosted as desired by addition of the amino acid to the culture media. Using a prototrophic variant of a particular strain of *B. subtilis* (*B. subtilis* WB600pPA101-1), alanine stimulated PA expression (whilst tryptophan inhibited it).

In addition, since catabolite repressor activity appears to be important, the organism is suitably cultured in a medium which lacks sugars such as glucose, which invoke this activity. A preferred carbon source is glycerol.

Recombinant microorganisms as described above may be prepared using conventional technology. The desired nucleic acid sequences may be incorporated into one or more suitable expression vectors and these vectors used to transform a host strain, in particular a prokaryotic host such as *B. subtilis*.

For example, the available plasmid vector pUB110 may be used to clone the gene encoding PA into a strain of *B. subtilis* as described for example by B. E Ivins et al., supra., and the resultant strain further modified as described above.

Nucleotide sequences prepared and vectors for use in this process form a further aspect of the invention.

The invention will now be particularly described by way of example with reference to the accompanying drawings in which:

FIG. 1 illustrates the structure of pPA101-1;

FIG. 3 shows the results of PA expression from the pag gene in pPA101-1 in different genetic backgrounds.

Figure 2:
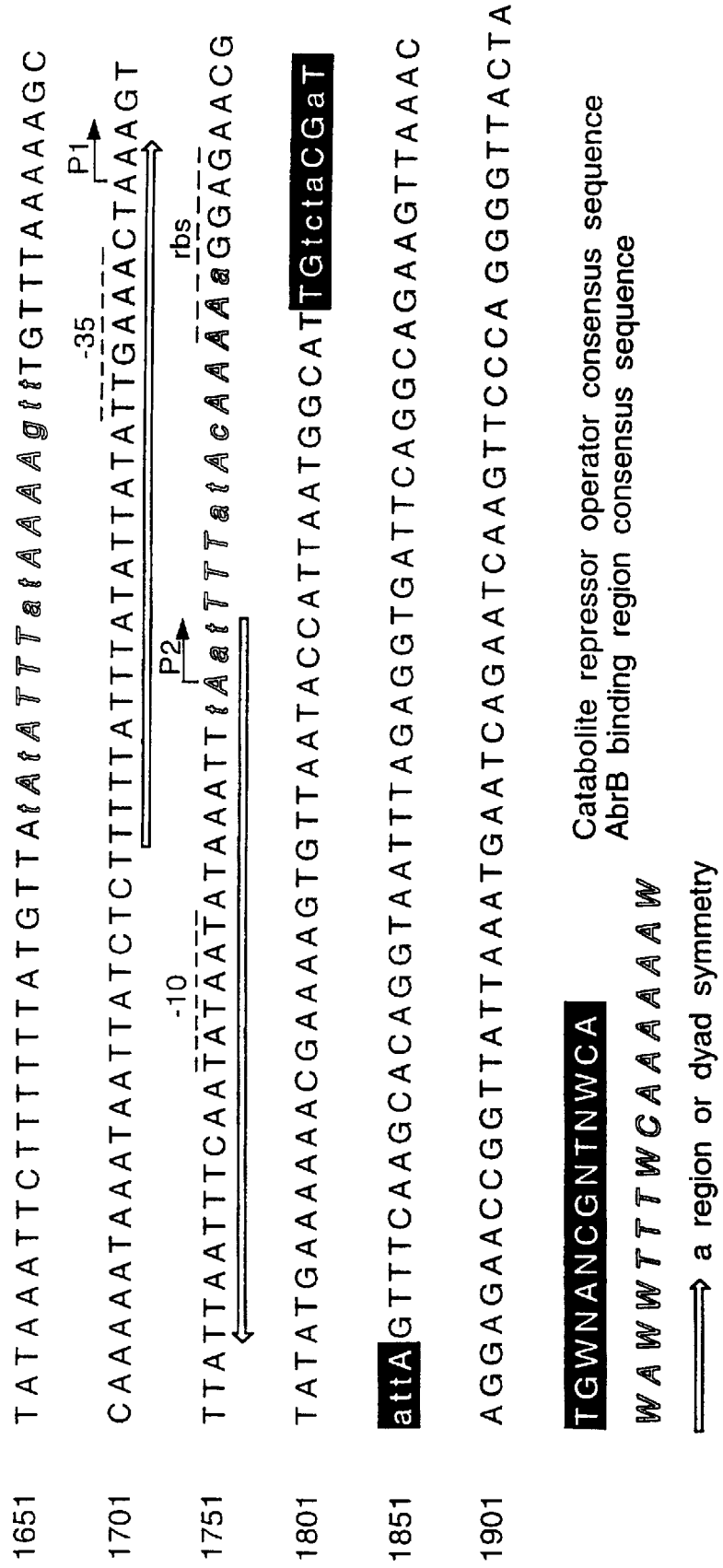
FIG. 2 shows a partial sequence of the PA gene (SEQ ID NO: 1), catabolite repressor operator (SEQ ID NO: 2) and noted region (SEQ ID NO: 3)

In the following Examples, the strains and plasmids referred to are shown in Table 1.

TABLE 1

| Strain/plasmid | Phenotype | Reference/Source |
| --- | --- | --- |
| *B. subtilis* | | |
| WB600 | trpC2, ΔnpreE, Δapre EΔepr, bpf, mpr::ble, nprB::ery | Xu-Chu Wu et al., (1991) supra. |
| IA 147 | alsA1*, alsR1, ilvΔ1, trpC2 | BGSC† |
| 1A172 | ilvΔ1, trpC2 | BGSC |
| JH642 | trpC2, pheA1 | Perego et al (1988) supra. |
| JH12575 | trpC2, pheA1, abrB::Tn917 | Perego et al (1988) supra. |
| Plasmids | | |
| pPA101 | Km$^r$; PA$^+$‡ | Ivins et al., (1986) supra |
| pPA102 | Km$^r$; PA$^+$ | Ivins et al., (1986) supra |
| pPA101-1 | Km$^r$; PA$^+$ | Example 1 below |

*alsA and ccpA genes are allelic (Henkin et al., Molecular Microbiology, (1991) 5, 575–584)
†Bacillus Genetic Stock Center, The Ohio State University, Columbus, Ohio, USA.
‡Protective Antigen

EXAMPLE 1

Production of Plasmid pPA101-1

A new plasmid pPA101-1 was derived from pPA101 following tranformation into *B. subtilis* WB600 using the protoplast method of Chang and Cohen (MGG (1979) 168, 111–115) with appropriate antibody selection. Plasmids were isolated from transformants and purified for sequencing using the QIAgen plasmid purification kit (QIAgen Inc. Chatsworth, USA).

Comparison of the restriction maps of pPA101 (Ivins et al. 1986, supra.) show that approximately 1.7 kb of DNA, from the vector and the 5' region of the PA-containing insert, had been deleted resulting in a plasmid similar in size to pPA102 (6.1 kb)

Nucleotide sequencing was performed by cycle sequencing in a Catalyst Molecular Biology LabStation using a ABI PRISM™ Dye Terminator Cycle Sequencing Ready Reaction Kit with AmpliTaq Polymerase FS. This was followed by electrophoresis in a 373A DNA Sequencing System (Applied Biosystems). Sequence data were analysed using the EditSeq programme option of the DNAstar Inc computer package (Abacus House, West Ealing, London, W13 0AS).

The published PA gene sequence (Welkos et al. Gene (1988) 69, 287–300) was used to design sequencing primers. The sequence determined in one strand was fully overlapped. When ambiguities occurred, they were resolved by sequencing the complementary strand.

This exercise revealed that the sequence of the vector/PA insert junction regions of pPA101-1 and pPA102 were identical. Analysis of this junction region showed the presence of a single copy of a 5 base sequence, TCTAT, which has been shown previously to occur in both pUB110 (complement of positions 1838–1842) and in the PA sequence (positions 1640–1644) (FIG. 1). The sequences flanking this junction corresponds to those expected if the DNA between the two TCTAT sequences had been deleted.

The sequence encoding the PA protein in pPA101-1 differed in only one base from the published sequence. Using the numbering system of Welkos et al., 1988 supra, a single base change was found at positions 2743 (G to C) which would change a GAA codon to a CAA codon (glutamic acid to glutamine).

The original PA-encoding clones pPA101 and pPA102 are based on the plasmid pUB110. This plasmid replicates via a single-stranded dexoyribonucleic acid intermediate by a rolling-circle replication mechanism (Gruss et al. Microbiological Reviews (1989) 53, 231–241). Such plasmids are particularly prone to deletion events such as homologous recombination between relatively short repeats (3 to 13 bases), which can result in the loss of several thousand bases (Ehrlich et al. Genetic Engineering, ed. J. K. Setlow et al. (1986) vol. 8, p71–83 Plenum publishing Corp., New York). Although both plasmids contained deletions, the junction points between vector/insert had not been defined. The data here suggest that pPA101-1, which was originally derived from pPA101, may have arisen as a consequence of recombination events between two TCTA sequences, leading to its present form which appears to be similar to pPA102.

EXAMPLE 2
Effect of an abrb Mutation on PA Expression

Strains JH12575 (AbrB) and JH642 (AbrB+) were transformed with pPA 101-1 using the protoplast method of Chang and Cohen (MGG (1979) 168, 111–115). The transformed strains were then grown.

Culture conditions and media for AbrB repression studies have been described previously (L. W. J. Baillie et al., Proceedings of the International Workshop on Anthrax Sept 19–21, 1995, Winchester, UK. Salisbury Med. Bull. 1996 87 (special suppl.) 133–135. Briefly 100 ml of culture medium in a 250 ml screw-capped Duran bottle was inoculated with 0.1 ml of a suspension of the organism in saline ($OD_{540}$ 1.3). A rich culture medium based on yeast extract and tryptone was employed (Fahnestock et al., J. Bacteriol. (1986), 165, 1011–1014). Specifically the medium contained per litre of deionised water, Bacto yeast extract (Difco) (20g), Tryptone (Difco) 33 g, NaCl 7.4 g $Na_2PO_4$ 8 g, $KH_2PO_4$4 g and L-histidine 1 g. The pH was adjusted to 7.4 and the medium was sterilised by autoclaving at 115° C. for 15 minutes. The medium in which plasmid-containing strains were cultured was supplemented with the appropriate antibiotic (kanamycin—final concentration 10 mg $1^{-1}$).

Cultures were incubated with shaking (150 rev $min^{-1}$) at 37° C. The progress of growth was monitored by optical density ($OD_{540}$ and was continued until the cultures reached late log/stationary phase growth ($OD_{540}$ of 1) at which time a sample of culture supernatant was assayed for PA.

The resultant solutions were assayed for PA by ELISA as described by Ivins et al. (1986) supra. The initial binding antibodies were rabbit polyclonal anti-PA. Human polyclonal anti-PA IgG was used to bind captured PA. PA/antibody complex was detected using goat anti-human horse radish peroxidase conjugate (Sera-Lab Ltd, Sussex), and developed with 2,2' azino-bis(3-ethylbenzthiazoline-6-sulphonic acid) substrate. PA values for the individual strains were determined as follows: cultures were grown to an $OD_{540}$ of approx. 1. Culture supernatants were assayed for PA by ELISA and the data normalised to a culture $OD_{540}$ of 1.0. Due to the possibility of plate to plate variation and a shortage of purified reference PA, the PA values for each mutant and its otherwise isogenic parent were determined on the same ELISA plate. Mean values were based on 8 or more assays per sample. The non-specific background mean, measured in an otherwise isogenic strain lacking the PA gene, was then subtracted. The data were analysed statistically and the results are illustrated in FIG. 3 section (a).

It is clear that 8-fold more PA ($P<0.05$, mean of the two determinations) was produced from the abrb strain.

EXAMPLE 3

Effect of a ccpA Mutation on PA Expression

Following the procedures described in Example 2 above, pPA101-1 was transformed into a Ccpa strain, IA147, and the otherwise isogenic parent strain IA172. The culture process and analysis were similar to those described in Example 2 except that the medium formulated for this study contained per litre of deionised water, Tryptone (Difco) 20 g, $K_2HPO_4$ (7 g), $KH_2PO_4$ (3 g), $(NH4)_2SO_4$ (1 g), sodium citrate (0.5 g), $MgSO_4 \cdot 7H_2O$ (100 mg) and L-histidine 1 g. The pH was adjusted to 7.4 and the medium was sterilised by autoclaving at 115° C. for 15 minutes. Following autoclaving sterile glucose wa added to a concentration of 2%.

The results are shown in FIG. 3*b* and illustrate that in a CcpA-background and in a tryptone based medium, there was a three-fold increase in the level of PA expression ($P<0.05$, mean of two determinations).

EXAMPLE 4

Effect of Amino Acids on PA Expression

To study the effect of amino acids on PA expression from a prototrophic strain of *B. subtilis* WB600 p101-1, the organism was grown in basal minimal medium (BMM) supplemented with tryptophan (150 mg/ml) and in BMM supplemented with a 16 amino acid mixture (M. R. Atkinson et al., J. Bacteriol (1990) 172, 4758–4765).

The BMM contained per litre of deionised water: $K_2HPO_4$, (7 g), $KH_2PO_4$ (3 g), sodium citrate (0.5 g) $MgSO_4 \cdot 7H_2O$ (100 mg), $(NH_4)_2SO_4$ (2 g), glycerol to 2% (w/v), L-histidine (1 g), uracil (1.4 mg), adenine sulphate (2.1 mg), thiamine HCl (1 mg), $CaCl_2$(10 mg), $FeSO_4 \cdot 7H_2O$ (2.5 mg), $ZnSO_4 \cdot 7H_2O$ (2.5 mg), $MnSO_4 \cdot 3H_2O$ (2.5 mg) and $H_2SO_4$ (0.1N). The pH was adjusted to 7.4 and the medium was filter sterilised using a 0.2 $\mu$m filter (German Sciences, Ann Arbor, Mich., USA).

The 16 amino acid mixture, which was added to the BMM where required contained L-cysteine (40 $mgl^{-1}$), L-arginine HCl (400 $mgl^{-1}$, L-isoleucine (200 $mgl^{-1}$), L-valine (200 $mgl^{-1}$), L-glutamate (800 $mgl^{-1}$), L-lysine (100 $mgl^{-1}$), L-phenylalanine (100 $mgl^{-1}$), L-proline (100 $mgl^{-1}$),L-threonine (100 $mgl^{-1}$), L-asparate (665 $mgl^{-1}$), L-alanine (445 $mgl^{-1}$), glycine (375 $mgl^{-1}$), L-serine (525 $mgl^{-1}$), L-tryptophan (150 $mgl^{-1}$), L-methionine (160 $mgl^{-1}$) all from filter sterilised stocks.

The culture conditions for PA expression were as follows: 100 ml of medium in a 250 ml screw-capped Duran bottle was inoculated with 0.1 ml of a suspension of the organism in saline ($OD_{540}$1.3). Cultures were incubated with shaking (150 rev $min^{-1}$) at 37° C. The progress of growth, monitored by optical density ($OD_{540}$, was continued until the cultures reached late log/stationary phase growth at which time a sample of culture supernatant was assayed for PA. When plasmid-containing strains were cultured the medium was supplemented with the appropriate antibiotic: kanamycin (final concentration 10 mg/l).

The time course of PA expression was determined by taking samples at hourly intervals during the course of culture and assaying them for PA. Samples were assayed for PA by ELISA as described in Example 2 above.

The PA content of the culture supernatant was determined by ELISA and the specific activity (mean ELISA—determine PS absorbance, $A_{412}$ per optical density unit ($OD_{540}$) was determined.

The results showed that there was a 3.6 fold reduction (p>0.5, mean of two determinations) in the level of PA expression when the organism was grown in the presence of the amino acid mixture.

EXAMPLE 5
Nucleotide Sequence Search for Negative Regulator Binding Sites

A region of the published nucleotide sequence of PA from base 1600 to 2000 which contains the promoter region and the first 195 bases of the structural gene was screened for homology with the consensus sequence, TGWNANCGNTNWCA, which codes for the catabolite repressor operator (M. J. Wieckert et al., Proc. Natl. Acad. Sci. USA (1990) 78, 6238–6242) and WAWWTTTWCAAAAAAW, a 16 bp consensus sequence based on 20 observed AbrB binding regions (M. A. Strauch et al., J. Bacteriol. (1995) 177, 6999–7002).

This programme allows a selected sequence to be searched for a particular site pattern or matrix sequence.

This resulted in the identification of sites which are homologous to the catabolite repressor binding site as well as the abrB binding site as illustrated by underlining in FIG. 3.

Hence inhibition of catabolite repressor protein and/or AbrB within the organism, for example by insertion mutagenesis of the gene encoding these proteins, or by adjusting the media accordingly, or by mutation of the binding sites as outlined hereinbefore would increase the yield of PA.

EXAMPLE 6

Purification and Efficacy of Recombinant PA

Recombinant protective antigen (rPA) was purified to homogenity from *Bacillus subtilis* using the following method.

rPA was fractionated from cell culture supernatant with ammonium sulphate followed by ion exchange chromatography on FPLC MonoQ HR 10/10 and finally gel filtration chromatography on FPLC Superose 10/30, yielding 7 mg rPA per litre culture. Homogeneous recombinant PA was characterised in terms of native and subunit molecular weight, and isoelectric point.

The protective efficacy of rPA against airborne challenge with the AMES strain of *B. anthracis* was determined in the presence of the adjuvants: Alhydrogel and RIBI. Maximum protection was achieved when rPA was adjuvanted with RIBI, in the guinea pig model.

What is claimed is:

1. A recombinant microorganism which is able to express *Bacillus anthracis* protective antigen which is able to generate an immune response in a mammal which response is protective against *Bacillus anthracis*, said microorganism comprising a sequence which encodes PA wherein at least one of (i) a gene of said microorganism which encodes a catabolic repressor protein (CcpA) and/or a transition state regulator, AbrB, is inactivated, and/or (ii) a region of the said PA sequence which acts as a catabolic repressor biding site is mutated so that it is inactivated; and/or (iii) a region of said PA sequence which acts as an AbrB binding site is mutated so that it is inactivated.

2. A microorganism according to claim 1 which comprises a *Bacillus subtilis*.

3. A microorganism according to claim 1 wherein a region of the said PA sequence which can act as a catabolic repressor binding site is inactivated.

4. A microorganism according to claim 1 wherein a region of the PA sequence which can act as an AbrB binding site is inactivated.

5. A process for producing *Bacillus anthracis* protective antigen which produces an immune response protective against *Bacillus anthracis* infection, which process comprises culturing a recombinant microorganism which is able to express *Bacillus anthracis* protective antigen which is able to generate an immune response in a mammal which response is protective against *Bacillus anthracis*, said microorganism comprising a sequence which encodes PA wherein at least one of (i) a gene of said microorganism which encodes a catabolic repressor protein (CcpA) and/or a transition state regulator, AbrB, is inactivated, and/or (ii) a region of the said PA sequence which acts as a catabolic repressor binding site is mutated so that it is inactivated; and/or (iii) a region of said PA sequence which acts as an AbrB binding site is mutated so that it is inactivated and recovering PA therefrom.

6. A process for producing PA which process comprises culturing a microorganism which is able to express PA in the absence of a carbon source which invokes catabolite repressor activity.

7. A process for preparing a recombinant microorganism according to claim 66 which process comprises transforming a microorganism with a vector comprising a sequence encoding PA which produces an immune response protective against *Bacillus anthracis* infection, wherein either (i) a gene which encodes a catabolic repressor protein and/or AbrB in said microorganism is inactivated; and/or (ii) a region which acts as a catabolic repressor binding site and/or a region which acts as an AbrB binding site in the said sequence encoding PA is mutated so that it is inactivated.

8. A nucleotide sequence which encodes PA which produces an immune response protective against *Bacillus anthracis* infection said sequence encoding PA wherein a region which acts as catabolic repressor binding site is inactivated and/or a region which acts as an AbrB binding site is inactivated by insertion mutagenesis.

9. A vector comprising a nucleotide sequence according to claim 8.

10. A recombinant microorganism which is able to express *Bacillus anthracis* protective antigen which is able to generate an immune response in a mammal which response is protective against *Bacillus anthracis*, said microorganism comprising a sequence which encodes PA wherein at least one of (i) a gene of said microorganism which encodes a catabolic repressor protein (CcpA) and/or a transition state regulator, AbrB, is inactivated, and/or (ii) a region of the said PA sequence which acts as a catabolic repressor biding site is mutated so that it is inactivated; and/or (iii) a region of said PA sequence which acts as an AbrB binding site is mutated so that it is inactivated, wherein said gene which encodes a catabolic repressor protein and/or AbrB is inactivated by insertion mutagenesis.

11. A recombinant microorganism which is able to express *Bacillus anthracis* protective antigen which is able to generate an immune response in a mammal which response is protective against *Bacillus anthracis*, said microorganism comprising a sequence which encodes PA wherein at least one of (i) a gene of said microorganism which encodes a catabolic repressor protein (CcpA) and/or a transition state regulator, AbrB, is inactivated, and/or (ii) a region of the said PA sequence which acts as a catabolic repressor biding site is mutated so that it is inactivated; and/or (iii) a region of said PA sequence which acts as an AbrB binding site is mutated so that it is inactivated, wherein said microorganism comprises a *Bacillus subtilis* and said gene which encodes a catabolic repressor protein and/or AbrB is inactivated by insertion mutagenesis.

12. A microorganism of claim 10 or claim 11 wherein the inserted sequences comprise a selection marker gene.

13. A microorganism according to claim 12 wherein the selection marker gene is an erythromycin resistance gene.

14. A microorganism of claim 10 or claim 11 wherein said catabolic repressor binding site comprises a region of the PA gene located between bases 1842–1854 of the full length gene which are bases 191 to 204 of SEQ ID NO: 1.

15. A recombinant microorganism which is able to express *Bacillus anthracis* protective antigen which includes at least one antigenic determinant thereof which is able to generate an immune response in a mammal which response is protective against *Bacillus anthracis*, said microorganism comprising a sequence which encodes PA wherein at least one of (i) a gene of said microorganism which encodes a catabolic repressor protein (CcpA) and/or a transition state regulator, AbrB, is inactivated, and/or (ii) a region of the said PA sequence which acts as a catabolic repressor biding site is mutated so that it is inactivated; and/or (iii) a region of said PA sequence which acts as an AbrB binding site is mutated so that it is inactivated, said microorganism comprising a CcpA⁻ or an ArbB⁻ mutant strain.

16. A recombinant microorganism which is able to express Bacillus anthracis protective antigen which is able to generate an immune response in a mammal which response is protective against Bacillus anthracis, said microorganism comprising a sequence which encodes PA wherein at least one of (i) a gene of said microorganism which encodes a catabolic repressor protein (CcpA) and/or a transition state regulator, AbrB, is inactivated, and/or (ii) a region of the said PA sequence which acts as a catabolic repressor biding site is mutated so that it is inactivated; and/or (iii) a region of said PA sequence which acts as an AbrB binding site is mutated so that it is inactivated, wherein a region of the PA sequence which can act as an AbrB binding site is inactivated and said AbrB binding site comprises a region of the PA gene located between bases 1778–1792 of the full length gene which are bases 127–142 of SEQ ID NO: 1.

17. A recombinant microorganism which is able to express Bacillus anthracis protective antigen which is able to generate an immune response in a mammal which response is protective against Bacillus anthracis, said microorganism comprising a sequence which encodes PA wherein at least one of (i) a gene of said microorganism which encodes a catabolic repressor protein (CcpA) and/or a transition state regulator, AbrB, is inactivated, and/or (ii) a region of the said PA sequence which acts as a catabolic repressor biding site is mutated so that it is inactivated; and/or (iii) a region of said PA sequence which acts as an AbrB binding site is mutated so that it is inactivated, wherein a region of the said PA sequence which can act as a catabolic repressor binding site is inactivated and inactivation of said catabolic repressor binding site and/or AbrB binding site is effected by mutation.

18. A process for producing Bacillus anthracis protective antigen which produces an immune response protective against Bacillus anthracis infection, which process comprises culturing a recombinant microorganism which is able to express Bacillus anthracis protective antigen which is able to generate an immune response in a mammal which response is protective against Bacillus anthracis, said microorganism comprising a sequence which encodes PA or said variant or fragment thereof wherein at least one of (i) a gene of said microorganism which encodes a catabolic repressor protein (CcpA) and/or a transition state regulator, AbrB, is inactivated, and/or (ii) a region of the said PA sequence which acts as a catabolic repressor binding site is mutated so that it is inactivated; and/or (iii) a region of said PA sequence which acts as an AbrB binding site is mutated so that it is inactivated and recovering PA therefrom, wherein at least one amino acid which stimulates PA expression is added to the culture medium of the organism.

19. A process according to claim 18 wherein said amino acid is alanine.

20. A process for producing Bacillus anthracis protective antigen which produces an immune response protective against Bacillus anthracis infection, which process comprises culturing a recombinant microorganism which is able to express Bacillus anthracis protective antigen or said variant or fragment thereof which is able to generate an immune response in a mammal which response is protective against Bacillus anthracis, said microorganism comprising a sequence which encodes PA wherein at least one of (i) a gene of said microorganism which encodes a catabolic repressor protein (CcpA) and/or a transition state regulator, AbrB, is inactivated, and/or (ii) a region of the said PA sequence which acts as a catabolic repressor binding site is mutated so that it is inactivated; and/or (iii) a region of said PA sequence which acts as an AbrB binding site is mutated so that it is inactivated and recovering PA therefrom, wherein the microorganism is cultured in the presence of glycerol and in the substantial absence of glucose.

21. A process for producing PA which process comprises culturing a microorganism which is able to express PA in the absence of a carbon source which invokes catabolite repressor activity, wherein glycerol is used as the carbon source in the culture medium.

22. A recombinant microorganism comprising Bacilltis subtilis which is able to express Bacillus anthracis protective antigen (PA), said microorganism comprising a sequence which encodes PA and wherein a member selected from the group consisting of a gene of said microorganism which encodes a catabolic repressor protein (CcpA) or a gene which encodes a transition state regulator, AbrB, is inactivated by insertion mutagenesis.

23. A microorganism according to claim 22 wherein the inserted sequence comprises a selection marker gene.

24. A microorganism according to claim 23 wherein the selection marker gene is an erythromycin resistance gene.

25. A recombinant microorganism comprising a Ccpa³¹ or an AbrB⁻ mutant strain of Bacilius subtilis which comprises a sequences which encodes Bacillus anthracis protective antigen (PA), and which microorganism expresses PA.

26. A process for producing Bacillus anthracis protective antigen (PA), which process comprises culturing a recombinant microorganism comprising Bacillus subtilis which is able to express Bacillus anthracis protective antigen (PA), said microorganism comprising a sequence which encodes PA and wherein a member selected from the group consisting of a gene which encodes a transition state regulator, AbrB, is inactivated by insertion mutagenesis; and recovering PA therefrom.

27. A process according to claim 26 wherein at least one amino acid which stimulates PA expression is added to the culture of the organism.

28. A process according to claim 27 wherein said amino acid is alanine.

29. A process according to claim 28 wherein the microorganism is cultured in the presence of glycerol and in the substantial absence of glucose.

30. A process for producing Bacillus anthracis protective antigen (PA), which process comprises culturing a recombinant microorganism comprosing a CcpA⁻ or an AbrB⁻ mutant strain of Bacillus subtilis which comprises a sequence which encoddes Bacillus anthracis protective antigen (PA); and recovering PA therefrom.

31. A process according to claim 30 wherein at least one amino acid which stimulates PA expression is added to the culture medium of the organism.

32. A process according to claim 30 wherein said amino acid is alanine.

33. A process according to claim 30 wherein the microorganism is cultured in the presence of glycerol and in the substantial absence of glucose.

* * * * *